US006870913B2

(12) United States Patent
Narasimhan et al.

(10) Patent No.: US 6,870,913 B2
(45) Date of Patent: Mar. 22, 2005

(54) SYSTEM AND METHOD FOR COLLECTING, DISSEMINATING AND MANAGING INFORMATION USING A VOICE AND DATA BASE SYSTEM

(75) Inventors: Anand Narasimhan, New York, NY (US); Paul Meyer, Brooklyn, NY (US); Pamela R. Johnson, Washington, DC (US)

(73) Assignee: VOXIVA, Inc., Washington, DC (US)

( * ) Notice: Subject to any disclaimer, the term of this patent is extended or adjusted under 35 U.S.C. 154(b) by 0 days.

(21) Appl. No.: 09/925,557

(22) Filed: Aug. 9, 2001

(65) Prior Publication Data

US 2002/0172335 A1 Nov. 21, 2002

Related U.S. Application Data

(60) Provisional application No. 60/275,994, filed on Mar. 15, 2001.

(51) Int. Cl.[7] .............................................. H04M 11/00
(52) U.S. Cl. ...................................... 379/106.02; 705/2
(58) Field of Search ............................ 379/88.13, 88.14, 379/88.17, 88.18, 88.22, 106.02, 110.01; 600/300–301; 128/903–904; 705/2–3; 709/217–219; 707/3–6; 348/14.01

(56) References Cited

U.S. PATENT DOCUMENTS

| | | | | |
|---|---|---|---|---|
| 4,893,270 A | * | 1/1990 | Beck et al. .................... 700/90 |
| 5,553,609 A | * | 9/1996 | Chen et al. .................. 600/301 |
| 5,872,923 A | * | 2/1999 | Schwartz et al. ............ 709/205 |
| 5,997,476 A |   | 12/1999 | Brown |
| 6,088,429 A |   | 7/2000 | Garcia |
| 6,148,297 A | * | 11/2000 | Swor et al. ..................... 707/3 |
| 6,151,581 A | * | 11/2000 | Kraftson et al. ................ 705/3 |
| 6,192,112 B1 |   | 2/2001 | Rapaport et al. |
| 6,249,809 B1 | * | 6/2001 | Bro ............................ 709/217 |
| 6,385,589 B1 | * | 5/2002 | Trusheim et al. ............... 705/2 |

* cited by examiner

*Primary Examiner*—George Eng
(74) *Attorney, Agent, or Firm*—Morrison & Foerster LLP

(57) ABSTRACT

The present invention is directed to a system, components of the system, a method and components of the method for collecting, disseminating and managing information between a data/voice base network and an end user or system. The present invention comprising: (1) an end user device; (2) a device adapter; (3) management surface interface; (4) a series of programmable tools capable of carrying out a desired function; and (5) an information source. The present invention being adaptable to collect, disseminate and manage information relating to public health, financing, banking, E-government, commercial sales, commercial distribution, and others.

13 Claims, 10 Drawing Sheets shows illustrative block diagram of an embodiment of a system of the present invention.

FIG. 1 shows illustrative block diagram of an embodiment of a system of the present invention.

FIG. 2 shows illustrative block diagram of an embodiment of a voice data based system of the present invention.

FIG. 3 shows an illustrative telephonic user interface for performing an authorization inquiry.

"Welcome"

"Please enter your account number" (1)
Account number is entered.

"Please enter your password" (2)
Password is entered.

"You have 4 new messages" (3)

"For messages, press or say the number 1" (4)

"To submit your weekly disease report, press or say the number 2" (5)

FIG. 4

FIG. 4 shows an illustrative user computer interface for performing an authorization inquiry.

| Validation | |
|---|---|
| Last Name | Garcia (8) |
| Account Number | XXXXXX (9) |
| Password | YYYYYY (10) |
| (7) | |

FIG. 5 shows an illustrative telephonic user interface.

"Message 1" (11)
    "The Ministry of Health has issued a advisory warning of a new outbreak of measles in you r region. Please call the Ministry of Health immediately for more details."

"Message 2" (12)
    "John Smith tested positive for tuberculosis. Please contact the tuberculosis lab immediately for more details."

"Message 3" (13)
    "Happy birthday"

"Message 4" (15)
    "This is the Chief Epidemiologist. There is a new report of Cholera in your region. Have you seen any cases this week of cholera?" (16)

"To submit you response to this inquiry, please press or say 2." (17)

"Please indicate the number of cases of cholera that you have seen in you areas within the past 10 days by pressing the number key or combination of number keys on ours touch tone ad which corresponds to those numbers of cases." (18)

Since Dr. Garcia had seen six cases of cholera in his region, Dr. Garcia responds to the above inquiry by pressing the number 6 on his touch tone pad.

"To submit your weekly disease report, please press 3. For directory services, please press 0."

Dr. Garcia presses the number 3 on his touch tone pad.

"With respect to each of the following medical conditions, please press the number key or combinations of number keys on your touch tone pad which corresponds to the number of new cases you have seen with that particular medical condition within the past 7 days." (19)

"HIV"

Dr. Garcia responds by pressing the number 2 (20)

"Malaria" (21)

Dr. Garcia responds by pressing the number 4 (22)

"Small pox" (23)

Dr. Garcia responds by pressing the number 0 (24)

"Chicken Pox" (25)

Dr. Garcia responds by pressing the number 4 (26)

"Small Pox" (27)

Dr. Garcia responds by pressing the number 3 (28)

"This completes your weekly report" (29)

Dr. Garcia finishes the system by hanging up the telephone. (30)

FIG. 6 shows an illustrative block diagram of an embodiment of a voice data based system of the present invention.

FIG. 7 shows an illustrative block diagram of an embodiment of a voice data based system of the present invention.

FIG. 8 shows an illustrative block diagram of an embodiment of a voice data based system of the present invention.

SYSTEM AND METHOD FOR COLLECTING, DISSEMINATING AND MANAGING INFORMATION USING A VOICE AND DATA BASE SYSTEM

CROSS REFERENCE TO RELATED APPLICATION

This application claims priority from U.S. Provisional Application Ser. No. 60/275,994, filed Mar. 15, 2001.

BACKGROUND OF THE INVENTION

1. Field of Invention

The present invention relates generally to the field of data processing using a communication and data based system, and more specifically to a method of collecting, disseminating and managing information from one or more end users or systems through a voice/data base network.

2. Description of the Prior Art

Currently, there are data processing systems in areas of collaboration, communication and transaction. However, these systems do not focus on methods that work seamlessly through voice and data interfaces, and they do not use such systems to rapidly customize and deploy information in a highly scalable and reliable fashion, particularly in the areas of health management, disease surveillance, case management, commercial distribution, call centers and others.

U.S. Pat. No. 6,168,563 (the '563 patent) describes a system and method that enables a health care provider to monitor and manage the health condition of a patient. This patent describes a remotely programmable apparatus and set of programmable scripts that can be used to capture patient information. This information is sent to a health care provider over a communication network. The system disclosed in the '563 patent does not combine the use of voice and data in the interaction with the patient. It also does not teach the use of pre-existing, non-programmable communication devices such as telephones, as part of the system. Further, the system of the '563 patent does not describe collaborative mechanisms for interaction between patients, health workers, pharmaceutical suppliers and others who may be involved in the process of patient treatment, thereby neglecting a vital aspect of the health care process. Further, the system of the '563 patent does not teach surveying methods for surveying that allow one-to-many, many-to-one, and many-to-many communication and collaboration mechanisms.

U.S. Pat. No. 5,441,047 describes health-monitoring methods using visual communication methods. Such methods involve the use of captured audio-visual data through specific systems, which collect patient symptoms and anatomical details. They do not describe any collaboration, transaction, surveying or other communication methods.

U.S. Pat. No. 5,434,611 describes a system for communication between doctors and patients using a two-way television network. This patent describes a one-to-one communication system, and does not provide for more elaborate methods of communication and collaboration.

U.S. Pat. No. 5,390,238, describes a system and method for monitoring patients. This patent teaches methods for managing patients through networks, including telephone networks. However, it does not describe collaboration and communication systems through multiple health care workers, intermediaries or suppliers, nor does it teach methods for surveillance, data aggregation, one-to-many and many-to-many interactions.

U.S. Pat. No. 6,098,053, describes a system and method for electronic financial transaction management over public networks. While this system allows users to manage financial transactions, it uses mechanisms only accessible over data networks. Also, it does not describe user-system interaction involving collaboration and communication on a one-to-many or many-to-many basis, and does not teach methods for management of processes and work flows in complex financial transactions that require specific forms of intermediation, management and control.

The present invention overcomes the drawbacks of the prior art by combining voice and data based systems to provide an elaborate and efficient information processing system which allows one-to-one, one-to-many, many-to-one and many-to-many communications and collaborations.

SUMMARY OF INVENTION

The present invention is directed to a system, components of the system, a method, and components of the method for collecting, disseminating and managing information from one or more users or other systems through a voice/data base network. Specifically, the present invention comprises a system. The system further comprises a management service interface that enables the end user to access the various components of the system. Such components include information sources (e.g., databases) or tools. Specifically, the tools may include software or hardware capable of performing a desired function. A management element controls the manner by which each individual tool interacts with each other. A user may access the system of the present invention through a user device which is communicatively linked to a device adapter. The device adapter is communicatively linked to the management service interface.

The components of the present invention can be adapted to collect, disseminate and/or manage information relating to public health, call centers, supply chains, work flow or any social network organization having a need to collaborate, communicate or transact. Tables 1 and 2 below provide a list of non-limiting applications of the present invention in various areas.

TABLE 1

| Features of the Present Invention | Finance & Banking | E-government | Commercial Sales & Distribution |
|---|---|---|---|
| Voice Messaging | In addition to basic messaging, finance and banking officials can send and receive financial updates. Customers and the public can obtain or receive reminders, financial data, etc. | In addition to basic messaging, federal, state and local government officials can send or receive broadcast messages, alerts, etc. | In addition to using basic messaging, distributors, salespersons and outlets can send or receive new product information, product alerts, etc. |

TABLE 1-continued

| Features of the Present Invention | Finance & Banking | E-government | Commercial Sales & Distribution |
|---|---|---|---|
| Data Collection & Surveying | The financial and banking sector may conduct surveys and collect basic data online or over the phone. | Citizens can file complaints, report violations, etc. | Commercial companies can monitor sales, stock levels, delivery status, survey customer requirements, etc. |
| Transactions | Authorized users may make payments, transfer funds, submit loan applications, etc. | Citizens and public officials can file applications, tax forms, request services or conduct other transactions on-line or via the telephone. | Salespersons, outlets and other customers can order products, supplies or services, etc. |
| Data Retrieval | Authorized users may obtain information on status of accounts, payments, etc. | Authorized users can obtain information on the status of applications, etc. | Users can access delivery status and updates, schedules, etc over the phone or online. |
| Information Services | Professionals and the public can access libraries (databases) of basic financial information, answers to FAQ, etc. | Citizens and public officials can get weather reports, basic information, common forms, answers to FAQ, etc. | Professionals and public officials can access libraries (databases) of basic information. |
| Real-time Communication | Users can connect to financial hotlines and live operators. | Citizens and officials can access live operators & hotline support. | Users can access live operators or hotline support centers. |

TABLE 2

| Features of the Present Invention | Public Health | Clinical Management | Drug & Vaccine Supply & Logistics |
|---|---|---|---|
| Voice Messaging | Public health professionals can send and receive individual and broadcast messages concerning disease outbreaks, health alerts, etc. | Physicians and other health professionals can send & receive messages, send reminders and other information to each other and to patients. | In addition to using basic messaging, pharmacists, physicians, etc can send and receive new product information, alerts, etc. |
| Data Collection & Surveying | Health professionals can report cases, conduct surveys or collect other health related data. | Patients can report their health status, etc. Health professionals can report adverse events, conduct surveys, etc. | Managers and outlets can monitor delivery and stock levels, etc. |
| Transactions | | Physicians can order tests, refer patients, etc. online or on the phone. Patients can make appointments, fill prescriptions, etc. | Pharmacists can order vaccines, drugs and other medical supplies |
| Data Retrieval | Professionals can obtain lab results, case & other data. | | Medical professionals can obtain delivery updates and schedules, account-related data, etc. |
| Information Services | Professionals and public officials can access libraries (databases) of information, training support and other information. | Patients and health professionals can access health information. | Pharmacists, patients and others can obtain drug and vaccine-related information. |
| Real-time Communication | Health professionals can connect to hotlines or live operators. | Patients or professionals can access live operators or hotline support. | Pharmacists and others can connect to hotlines and operator support centers. |

Specific embodiments are not included for each of the applications identified in Tables 1 and 2. However,. it is understood that one of ordinary skill in the art can modify the present invention accordingly, based on the descriptions herein, to carry out and practice any of the applications listed in Tables 1 and 2.

The system of the present invention also provides one or more information sources (i.e., data bases), authentication rules or data pertaining to a sender and a recipient. The present system also provides the ability to generate, store or disseminate mapping information to one or more end user devices. The present system also includes one or more systems with programmatic capabilities uniquely defining the end user devices by identification number, location, connectivity status to a communication network, or by other means of identification.

In addition, the system of the present invention may provide one or more systems that enable connectivity between one or more end user devices through a communication network. The system of the present invention may also provide one or more systems that enable connectivity between one or more end users through one or more intermediaries, processes or systems which serve as moderators, authenticators or auditors for the exchange of information between a first sender and a first recipient.

These and other applications and advantages of the present invention will become more apparent after consideration of the ensuing description and accompanying drawings.

BRIEF DESCRIPTION OF THE DRAWINGS

For a further understanding of the nature and objects of the present invention, reference should be had to the following detailed description, taken in conjunction with the accompanying drawings, wherein:

FIG. 4 shows an exemplary user computer interface for performing an authorization inquiry in a health management environment;

FIG. 5 shows an exemplary telephonic exchange for the present invention in a health management environment;

Additional features and advantages of the invention, as well as the structure and operation of various embodiments of the invention, are described in detail below with reference to FIGS. 1 to 7. In FIGS. 2–7, reference numbers that correspond to an element in FIG. 1 are indicated by like numbers with adjacent letter (e.g., 130a, 130b, 130c etc.). Such like numbers indicate that the elements in the figures are functionally similar to each other.

DETAILED DESCRIPTION OF THE PRESENT INVENTION

The individual components of the present invention are commercially available computer, software, hardware and/or communication devices, each capable of performing the functions described herein.

Figure 1:
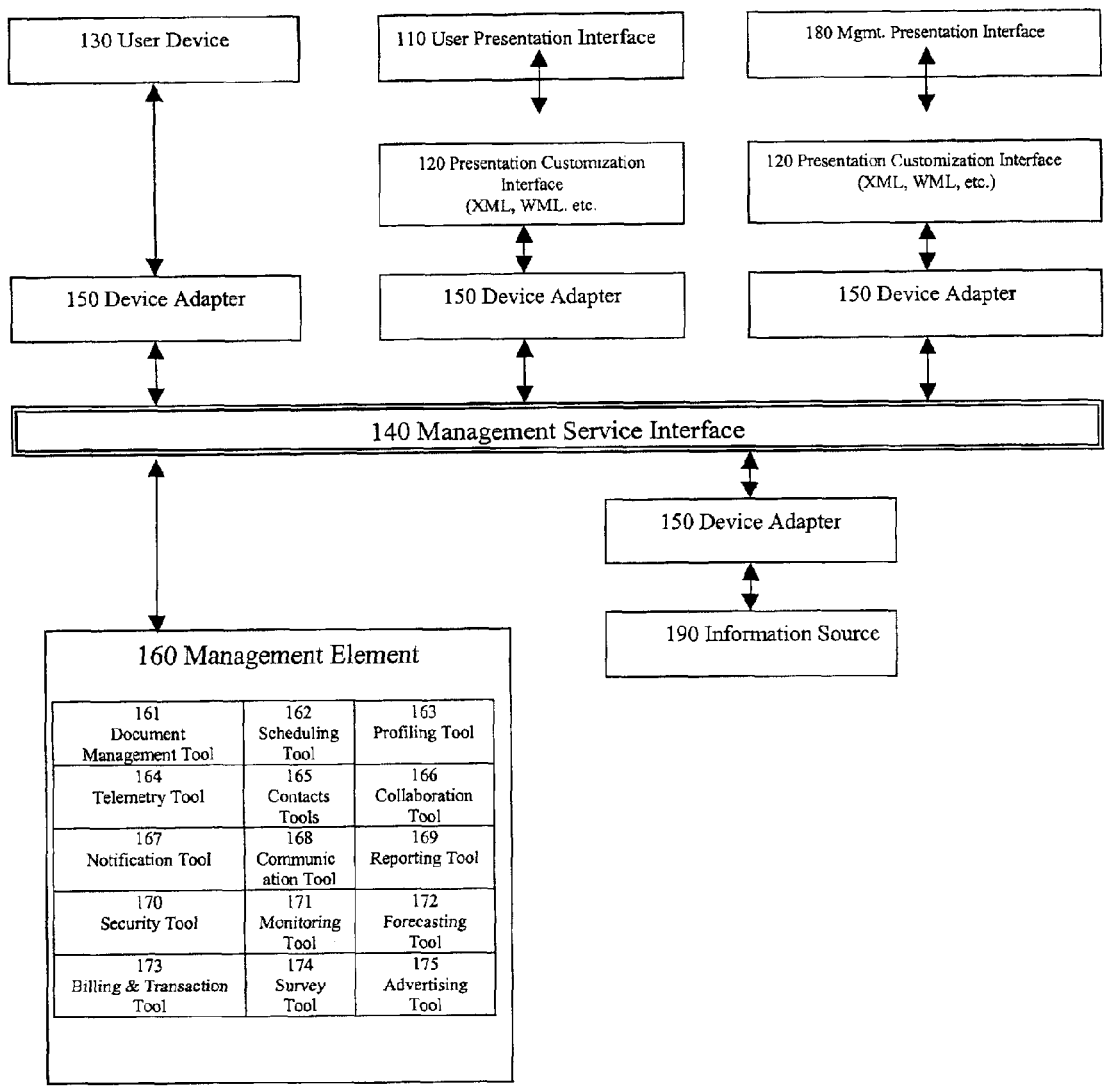
FIG. 1 shows an exemplary block diagram of an embodiment of a voice and data based system contemplated by the present invention applies.

FIG. 1 shows an exemplary block diagram of a voice and a data based system contemplated by the present system. Management Service Interface (MSI) 140 is a real-time messaging and communication interface coupled and/or linked to the other components of the present system. MSI 140 manages the flow of information between or among these components, which include but are not limited to, "Devices," "Device Adapters," "Tools" and "Management Elements." MSI 140 can be scaled efficiently to handle message flow without creating a bottleneck. For example, MSI (140) can function as a messaging interface. As such, MSI (140) can have the capability to schedule and prioritize messages and deliver them in real time. Suitable interfaces for use with MSI (140) include various products known in the art such as those produced by IBM (MQ) and Microsoft (MSMQ).

As used herein, user Device (130) includes any communication device that enables the user of the device to access the system of the present invention. Such device may include, but is not limited to, telephones, palm pilots, personal computers, pagers, fax machines, e-mail, web browser, to name a few. In the present invention, one or more user Devices can be communicatively coupled to each other and/or linked to MSI (140) through Device Adapter (150).

Device Adapter (150) is responsible for interfacing any user Device (130) or Tool (161–175) with MSI (140). The Device Adapter (150) may include software or hardware, or both. Suitable Device Adapters may include, but are not limited to, Interface Cards (Dialogic) capable of performing the desired functions herein.

As used herein, a "Tool" includes hardware or software capable of performing a desired function. Such Tools include, but are not limited to; Document Management Tool (161); Scheduling Tool (162); Profiling Tool (163); Telemetry Tool (164); Contacts Tool (165); Collaboration Tool (166); Notification Tool (167); Communication Tool (168); Reporting Tool (169); Security Tool (170); Monitoring Tool (171); Forecasting Tool (172); Billing and Transaction Tool (173); Survey Tool (174); and Advertising Tool (175). Each of these Tools are commercially available and discussed in detail below.

In the present invention, the Tools are linked to Management Element (160). As used herein, Management Element (160) includes software that controls the manner by which the Tools of the present invention interact with each other. For example, Management Element (ME) 160 contains the logic associated with managing the processes required for interaction between or among the various Tools.

ME 160 comprises a number of tools that serve specific purposes for manipulating information derived from MSI 140. Document Tool 161 provides a mechanism for managing multiple sets of structured or unstructured information (e.g., files, faxes, voice messages, images, notes, etc.). For example, Document Tool 161 may posses the capability to organize, access or archive information. Here, a user may access the system of the present invention via a Device 130, which can be a telephone. Through Device 130, the user may extract particular information from the system of the present invention according to a defined parameter, e.g. topic, date, or person's name. Document Tool 161 also manages the use of data markers to tag information. For instance, if a communication from an end user comprises of text, files, voice recordings and images, with contextual and time-sensitive sequencing, Document Tool 161 inserts data markers or tags specifically constructed to represent such information, so that future management of this information is efficiently handled. This also applies to multiple end users or administrators, and any data created or manipulated by them, as well as to multiple communications and versions. Text based data markers and tags are generally well understood in the art. Examples include the use of markup languages such as HTML, XML, etc., as well as database schemas that specifically manage structured and unstructures information (example, Oracle, SQLServer, etc.). In the system of the present invention, voice recordings or annotations can be used to identify information pertaining to an end user, or groups of end users, or a particular transaction. For example, an end user could record his name as a voice recording. This recording, with possibly some subsequent processing of the recording, can be used to uniquely identify the end-user as well as serve to tag all information pertaining to that end-user, or to any related transaction.

Scheduling Tool 162 manages the scheduling of events and information within the system of the present invention. For example, the elements in the system may be programmed to trigger a need for a specific event to occur (e.g., a health worker needs to be reminded to monitor a drug treatment for a patient). Scheduling Tool 162 manages the scheduling of such event. Scheduling Tool 162 may also provide a sophisticated calendaring system that is used to manage scheduled events, such as instructing a patient when to take his medication.

Profiling Tool 163 manages the information collected from end users or devices. For example, profile information collected from an end user, such as name, geographical location or medical condition, may be managed by Profiling Tool 163. Such information may include device specific information pertaining to the end user (e.g., type of device, time of use, registration, location characteristics etc.). This type of information can be extracted, managed and/or stored by Profiling Tool 163.

Telemetry Tool 164 manages data collected from various end user devices. This might include status messages from communication devices, location information from cellular phones, geographical information such as maps and coordinates to identify specific locations, etc. Contacts Tool 165 maintains information pertaining to contact information for various users, and may also be used for managing public or private contact lists, address books, telephone numbers, e-mail address, business telephone numbers, etc.

Collaboration Tool 166 creates and manages groups of users, which brings together a number of collaborative elements within the system of the present invention. For example, these collaborative elements may include group creation and management exchange of structured and unstructured voice and data content, as well as workflow management within groups of users, devices or systems.

Notification Tool 167 is responsible for generating notification messages for delivery to other components of the system. This tool is event drive. For example, Notification Tool 167 can be programmed to provide a predetermined notification function when the system receives a specific tape or category of information. Upon receipt of such information, Notification Tool 167 will interact with other tools causing an end user to be notified of the incoming information through Device Adapter 150 and User Device 130.

Communication Tool 168 prepares information for delivery between the various components of the present system. E-mail messages, faxes, voice messages or real-time communications between various components of the system are managed by this tool. For example, if an end user desires to send information within the present system via facsimile, Communication Tool 168 converts the information into a form suitable for facsimile transmission. If an end user desires to convert an e-mail message into voice mail, Communication Tool 168 converts the contents of the e-mail massage into a form suitable for delivery into voice mail.

Reporting Tool 169 generates and manages reports or compilations of data based on information from other system components. In operations, the Reporting Tool 169 collects, manipulates and organizes the information in a desired format. The information is then transmitted to a Device, another Tool or end user in the specified format.

Security Tool 170 provides security interfaces for interactions between other system components and end users. Security Tool 170 may have the capability to encrypt information. It may also have the capability to authenticate information flowing through the system of the present invention. Security Tool 170 may control access of information between or among end users, end user devices, tools and any management element.

Monitoring Tool 171 provides mechanisms for monitoring various aspects of system performance and maintenance of the present system. For example, monitoring tool 171 will alert system operators if another tool or any component of the present system is disabled or requires special repair.

Forecasting Tool 172 determines future action to be taken based on information gathered in the present system. For example, if the information acquired in the system indicates that occurrences of yellow fever in a particular area have increased ten fold, then Forecasting Tool 172 will determine that status reports for a particular area must be received by the responsible physicians every two hours for the next 4 to 6 weeks, depending on the information contained in the status reports.

Billing and Transaction Tool 173 provides mechanisms for billing end users and/or for creating and providing billing records for purposes of further manipulation by other billing systems that interface with the system of the present invention. The information managed by Billing and Transaction Tool 173 may include real time usage information transactional information and/or user information, such as number of users on the system, length of system usage, volume of data handled in a specific transaction, etc. Billing and Transaction Tool 173 also provides mechanisms for end users, devices and systems to engage in business transactions within the system, or with other systems that interface with the present invention.

Survey Tool 174 provides mechanisms for creating, delivering, and managing surveys to and from end users, devices or tools. For example, a doctor can compose a medical survey to send out to his health workers in the field. This survey could be a voice message, sufficiently annotated to present an interactive interface to each health worker, thereby creating a mechanism for the health workers to respond via data entry as well as via voice recordings.

Advertising Tool 175 creates and manages advertisements within the system or provided through other systems that interface with the present invention. These advertisements are typically delivered to Device 130, UPI 110 or ME 160. This is a powerful feature, especially since the other tools in ME 160 can be used to creatively target specific customers. For example, in a consumer distribution environment, targeted advertisements may be sent to consumers based on their profiles, which may include information about their usage or ownership of specific devices, purchase history, etc.

The present invention also comprises a user presentation interface (UPI) 110 and a Management Presentation Interface (MPI) 180. User Presentation Interface (UPI) 110 and Management Presentation Interface (MPI) 180 include, but are not limited to, presentation interfaces such as a web browser, micro browser, or a display on a cell phone, lap top, pager, computer monitor and the like. UPI 110 represents the interface used by an end user of the present system. MPI 180 represents an administration interface, which may include software capable of managing the configuration of the system. MPI 180 is typically used by an administrator of the system of the invention, for example, to manage end user accounts, user settings and profiles, privileges and permissions. The presentation of information from MSI 140 to UPI 110 or MPI 180 is managed via a "Presentation Customization Interface" (PCI) 120. Presentation Customization Interface (PCI) 120 represents any software or other means by which information is processed so that it can be displayed on UPI 110 and MPI 180. PCI 120 is typically a software or a representation language, examples of which are known in the art as markup languages (HTML, XML, WML, etc.) or other middleware that specifies a set of rules and methods for presenting the information through MSI 140 to a device (for example a device such as a computer browser or a pager or a cellular phone) with a specific presentation interface 110 or 180 (for example a presentation interface such as a web browser or a display on a pager or a display on a cellular phone).

The system of the present invention also provides elaborate mechanisms to enable information to be communicated with or transferred from an end user to the components of the present invention. For example, if Device 130 is equipped with a mechanism to communicate directly via a secure channel on a data network, Device 130 may transmit relevant data pertaining to its operation to MSI 140 via Device Adapter 150. MSI 140 then aggregates the information, allowing subsequent extraction of selected portions of the data from Tools 161–175 via ME 160. If Device 130 is equipped with communication capability (e.g., phone, computer, hand-held communication device, etc.), information including notification messages, electronic mail, data communication etc. can be sent from Device 130 to MSI 140 via Device Adapter 150. This information can then be used for subsequent communication with and/or transfer to one or more Tool, Device and/or network.

Information aggregated through MSI 140 is managed via ML 160, which may perform various functions. For example, ME 160 may manipulate information based on a pre-defined set of rules and/or learning algorithms to route, archive or retrieve information contained in IS (160) or third party information sources. ME (160) may also interact with various third party information sources to route or collect information in order to perform transactions, or to inform the end user or other devices or systems.

The system of the present invention also includes Information Source (IS) 190 which include a means for storing information, including data. IS 190 includes any available hardware, software, computer, main frame or any other electronic device having memory capabilities. The information stored in IS 190 may be derived from various sources. For example, the information may be accumulated through the operation of the present invention by one or more users or systems. In this instance, the information is stored in IS 190 as the information accumulates or is generated by the system. Information may also be provided by a third party or incorporated directly into the present system as an independent component or part of an existing component, including but not limited to, IS 190.

The information stored is referred to as a database. In one alternative embodiment of the present invention, the databases store information pertinent to or derived from data loaded in the present system and/or processed or accumulated by any of Tools 161–175.

It should be understood, however, that the invention is not limited to the particular database embodiment. Instead, the invention is adapted and intended to cover other database structures and organizations that are capable of storing information and information pertinent to the analysis of the information. The particular information that is stored in the databases is implementation dependent and varies based on a number of factors, including the type of analysis that is desired and the type and content of the information that is maintained in the present system.

Many of databases generated by the present system, such as medical databases, financial databases, person databases and customer databases, maybe loaded using information provided by the user of the system or a third party provider. After loading, these databases are updated as necessary. It should be understood that the present invention works equally well with data provided by any party as long as the data's format matches the format of the databases in the system. The information stored in the databases may be text, images, graphics, audio, video, multimedia or any other information that can be stored in electronic form.

The medical databases may include, but are not limited to, the following types of information:

Patient profile such as name, age, sex, date of birth or death, disease history, vaccination history Reports from health workers on specific incidents, such as laboratory results, case symptoms, or disease outbreaks. This information could be stored as data, or as voice recordings or image clips associated or tagged appropriately such as to be identified with the specific incident in question; and Geographical information such as location of patient, location of disease outbreak, or location of closest facility to handle a case or for a specific communication.

The customer databases may include, but are not limited to, the following types of information:

Customer profile, including name, address, financial and credit profile, etc.;

Purchase history, such as items bought, dates of purchase or return or exchange; and Frequency of purchase or re-purchase of supplies or goods.

Multiple IS 190's provide value added information to end users, systems or devices through device adapter 150 to MSI 140. This information may be subsequently processed via ME 160.

Having described various elements of the system of the present invention, along with specific applications thereof, other non-limiting applications of the present invention are described below. Although specific embodiments of the present invention have been described and illustrated herein, it is to be understood that a person skilled in the art can make modifications within the scope of the invention and apply it to other environments and/or uses including, but not limited to, microfinancing or any other financial transaction, such as banking and microlending. It may also be applied to commercial distribution networks, agricultural work flows or any other social network organization having a need to collaborate, communicate and transact. Other specific embodiments of the system described herein include, but are not limited to the following.

Health Management Application

Figure 2:
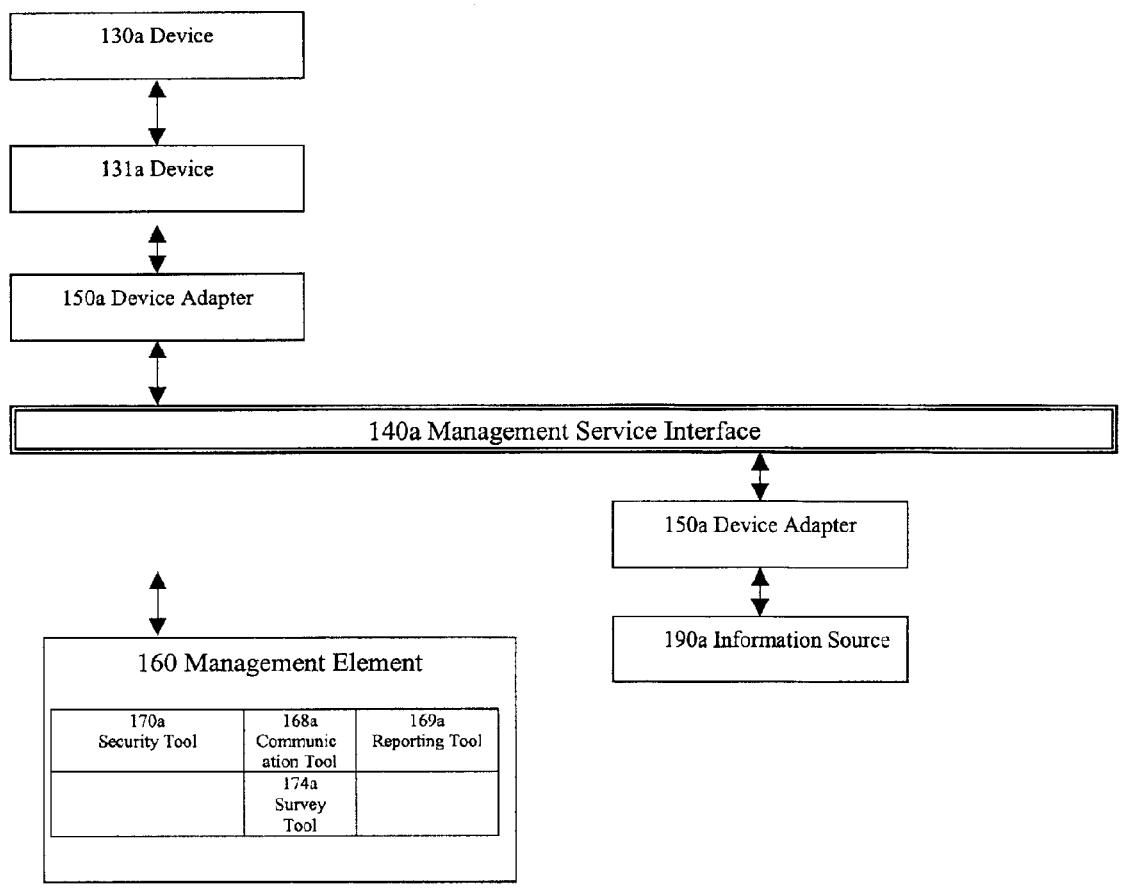
FIG. 2 shows an exemplary flow diagram of an embodiment of a voice and data based system contemplated by the present invention.
Figure 3:
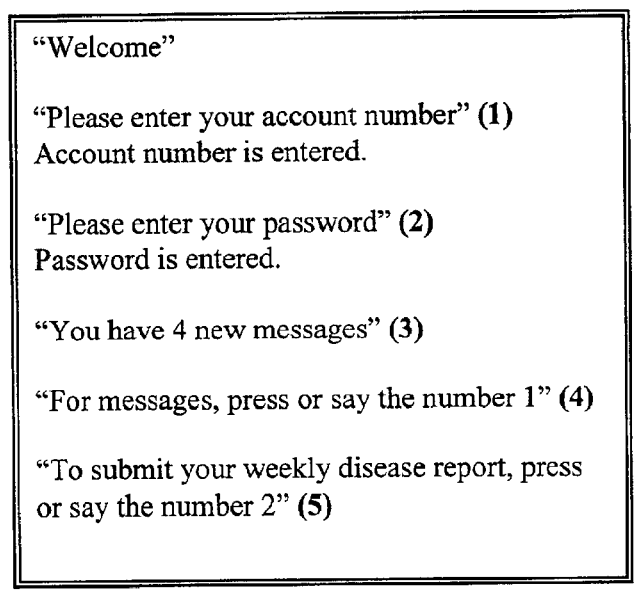
FIG. 3 shows an exemplary telephonic exchange for performing an authorization inquiry in a health management environment.

As stated previously, the present invention can be adapted to manage health information, such as reporting information concerning disease outbreaks, as well as monitoring the spread of diseases. FIG. 2 shows an exemplary flow diagram of an embodiment of the present invention applied in a health care environment. Specifically, unit 130a is a telephone, shared payphone or phone kiosk. Unit 131a is a computer, for example, a personal computer. The user (who may be a doctor in rural Peru) may use either or both of these devices to communicate to unit 150a, which is a telephone switch interface. The user may access unit 130a and use it to check voice mail and to submit his or her weekly disease report. FIGS. 2–5 illustrate the interaction between such a user and the system of the present invention. Here, the user first calls the system via unit 130a, which is connected to a telephone network system, through telephone switch interface unit 150a. Before the user can access the information in the system, he or she must be validated. FIGS. 3 and 4 show an illustrative telephonic interactive and computer interface, respectively, for performing a validation inquiry.

In FIG. 3, unit 168a, the Communication Interface Tool, presents the user with an interactive voice response menu, asking him or her to enter a pre-assigned account number (1) and authorization password (2). When the information is entered, Unit 170a validates the entry. Upon successful validation, an interactive voice response informs the user of the number of messages in voice mail (3), and then asks whether the user wants to retrieve the messages (4) or submit a weekly disease report (5).

In FIG. 4, user interface (6) includes a view of a constructive index card (7) to elicit specific information about the user. Here, the user must identify himself, herself or itself by a name (8), account number (9), and password (10). In FIG. 4, after the requested information is provided, Unit 170a determines whether or not authorization may be given to the user. Upon successful validation, in both FIGS. 3–4, a more sophisticated interface on the authorization process may be changed to require more or less information based on the information sought.

After the validation process is completed, unit 168a informs the user whether he or she has any new messages. For example, in FIG. 2, Unit 168a informs the user that he or she has 4 new messages (FIG. 5). When the user retrieves these messages, each message is retrieved from an information source 190a, through MSI 140a, to Communication Tool 168a. Each message is processed by 168a and delivered to telephone 130a via MSI 140a and 150a.

FIG. 5 shows an exemplary telephonic dialogue between the user and the present invention illustrated in FIG. 2. Here, the 4 messages are retrieved from IS 190a and played back to the user. Message 1 (11) is a health advisory from the Ministry of Health warning of a new outbreak of measles in the region. Message 2 (12) is from the Tuberculosis lab reporting the test results of a patient. Message 3 (13) is a personal message from the user's son. Message 4 (15) is a voice mail survey from the Chief Epidemiologist. Here, the user is asked whether he or she has seen any recent cases of cholera (16). The user is then asked to reply to this inquiry by pressing the number 2 on the touch tone telephone (17). In this example, the user had seen six cases of cholera in the region. The user responds to the inquiry by pressing the number 6 on the touch tone telephone pad. (18).

Message 4 in the FIG. 5 was created by the sender of the message through Survey Tool 174a. This message may be created using various interfaces. For example, telephone interface 130a can (record the sender's voice message and include specific annotations created by spoken voice commands and keypad entries. Another interface may include web-based interface on computer unit 131a, which allows the sender to compose the survey visually and record the voice components of the survey through a microphone interface attached to the computer.

After the user listens to all 4 messages, he or she is further prompted by Communication Tool 168a to answer a specific set of questions, through an interactive voice message interface, created by the information content from IS 190a, which contains specific annotations in the message, thereby causing Communication Tool 168a to create the specific set of questions. When he responds to these questions, his or her responses may be recorded as data entries, and subsequently manipulated by Reporting Tool 169a, and delivered to another IS 191.

After the user retrieves the voice mail messages, he or she is further prompted by Communication Tool 168(a) to submit a weekly disease report. This is performed through a specific set of questions, via an interactive voice message interface, created by the information center from IS 190(a), which contains specific annotations in the message, thereby causing Communication Tool 168a to create the appropriate set of questions. Continuing with the example illustrated in FIG. 5, the user is asked to report the number of new cases seen in a particular area, such as HIV, malaria, small pox and chicken pox. Here, with respect to each of these medical conditions the user is asked to press the number key or combinations of number keys on the touch tone pad which corresponds to the number of new cases seen within the past 7 days (19). For new cases of HIV, the user responds by pressing the number 2. For malaria, small pox and chicken pox the user responds by pressing the numbers 4, 0 and 4, respectively (20–30).

After pressing the messages and submitting the weekly disease report, the user hangs up the telephone, thus completing the progress: For example, the user's responses may be recorded as data entries, and subsequently manipulated by Reporting Tool 169a, and delivered to IS 191a. The information submitted may be instantly transmitted to the ministry of health database 192, and is accessible to several epidemiologists who can study the report, take decisive action to prevent further disease outbreaks, or follow-up with the user through a more elaborate set of voice messages or surveys using the components of the present invention.

Call Center Application

The present invention can also be adapted to function as a call center. Call centers typically employ a number of agents, connected through expensive call routing and switching equipment. When a call reaches a call center, the phone and voice response interface must often trigger activation of a screen display on a computer or web browser. Relevant details from databases pertaining to the caller (e.g., caller name, address, specific account information etc.) appear on the screen display so that the agent can address the caller's issues.

However, the operation of call centers are problematic. For instance, the interaction between the voice and data interfaces are complex and expensive. Also, they do not allow call center operators to be geographically dispersed and their centralized architectures do not allow for easy integration with third party databases and systems, thereby creating more inefficiencies, bottlenecks and security risks.

It is often preferable to have a distributed system, without the need for expensive switching, routing equipment and the constraints of inflexible interfaces. The present invention may be adapted to create distributed call center applications with easy integration of voice and data interfaces and simple access to third party databases and systems.

Figure 6:
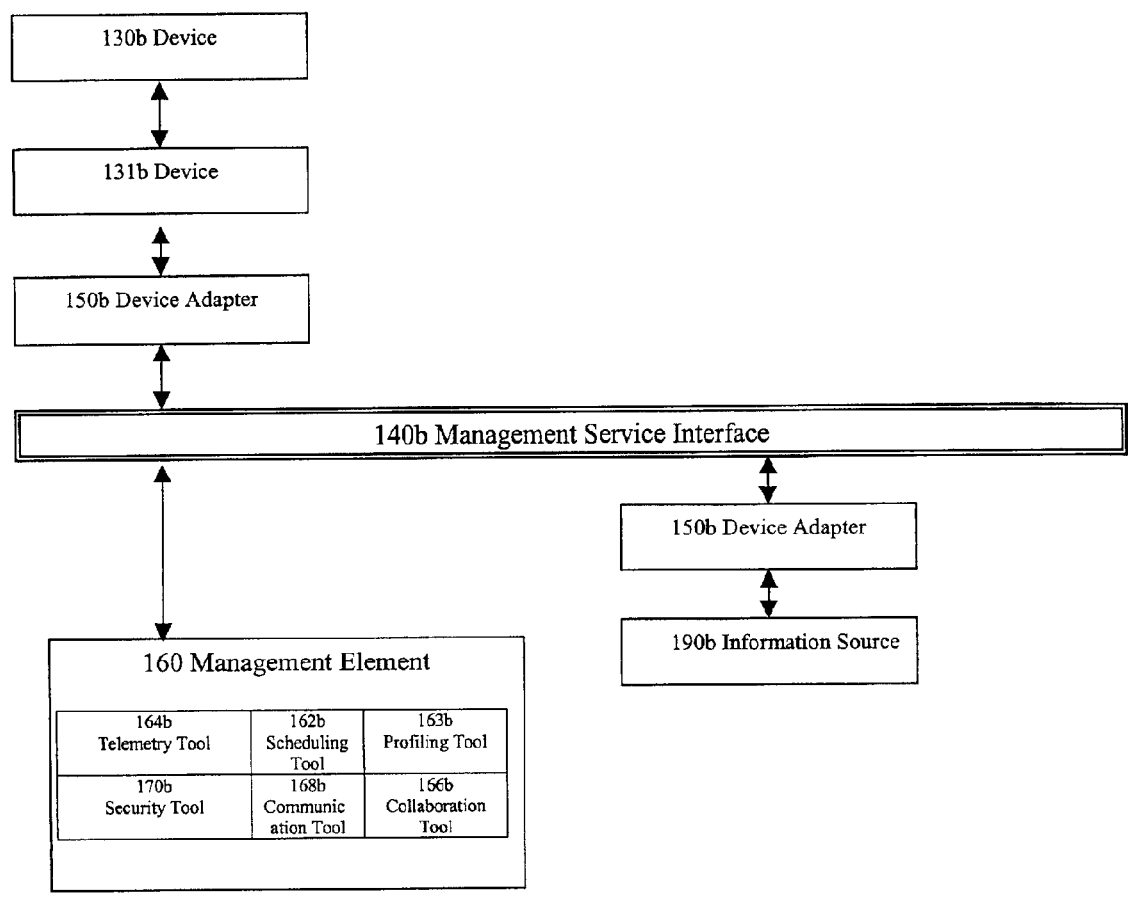
FIG. 6 shows an exemplary flow diagram of another embodiment of the voice and data based system contemplated by the present invention.

FIG. 6 shows an exemplary flow diagram of an embodiment of the present invention applied in a call center environment. In this example, unit 130b is a telephone used by a call center agent. Unit 131b is a computer or web browser interface also used by a call center agent. Each agent is registered into the system via Profiling Tool 163b for data collection and profiling and Telemetry Tool 164b for ongoing updates pertaining to connectivity status. Here, the computer used by one of the agents would contain identifying software that the agent would activate. The software would prompt the user to enter a username and password and deliver that information to Security Tool 170b for verification. Further, this identifying software, which is comprised of a listener and a transmitter, would continually update Telemetry Tool 164b of the status of the computer, and listen for any commands or signals from the other components in the system.

Further, there would be an association in Profiling Tool 163b and Telemetry Tool 164b, which identifies the telephone number of unit 130b, and indicating that it is the preferred voice interface for the agent using computer unit 131*b*. When a caller calls into the system from their phone, via communication interface 150*b*, and through Communication Tool 168*b*, the caller is prompted by the system using Communication Tool 168*b* and an interactive voice response interface, to enter relevant information that identifies the caller and the nature of the call. The system then uses a pre-defined set of rules in Collaboration Tool 166*b* and further uses Scheduling Tool 162*b* to determine where the call should be routed. Once this call is routed to unit 130*b*, and the call center agent answers the call, the Collaboration Tool 166*b* causes relevant caller information to be extracted by an information source 190*b*, and sends a message to the listener software on unit 131*b*, to activate a browser or other display means, and presents the extracted data to 131*b*. The call center agent can thus visually manage the caller's relevant records on their computer. Finally, when the session has ended, and the caller has hung up the phone, Telemetry Tool 164*b* senses the end of the call, and causes 166*b* Collaboration Tool to trigger the ending of the visual display session on unit 131*b*. Hence, an entire call center operation can be managed, in a completely distributed environment, utilizing the switching infrastructure of the telephone network, and efficiently utilizing the methods of the present invention.

Geographical Information System Application

The present invention is also applicable in a number of environments involving the use of geographical information systems, including but not limited to location of end users, suppliers, distributors and goods in a supply chain system, or location of patients, hospitals, doctors, pharmacies or medical supplies in a medical logistics application.

Figure 8:
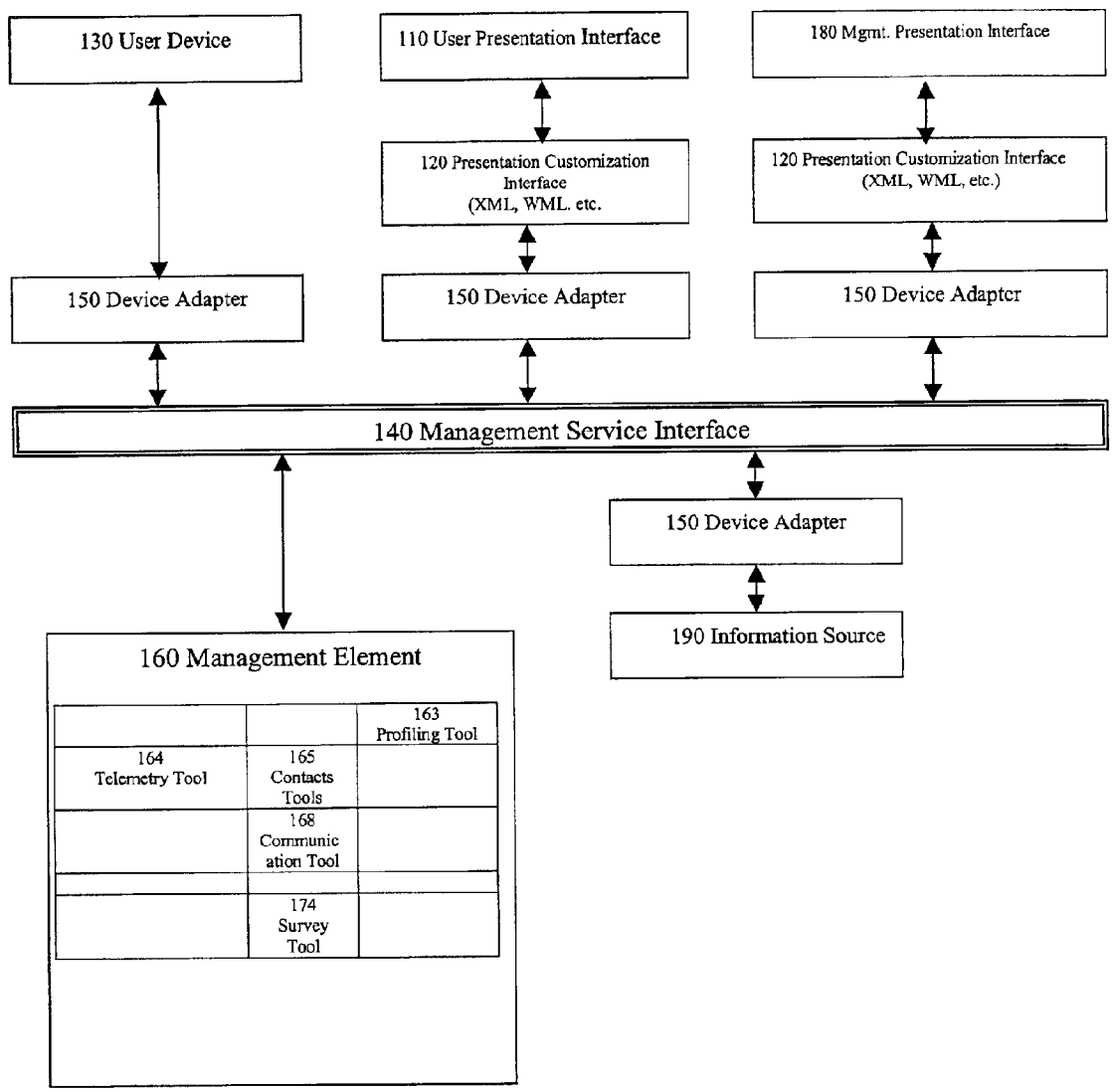
FIG. 8 shows a flow diagram of another embodiment of a voice and data based system contemplated by the present invention.
Figure 9:
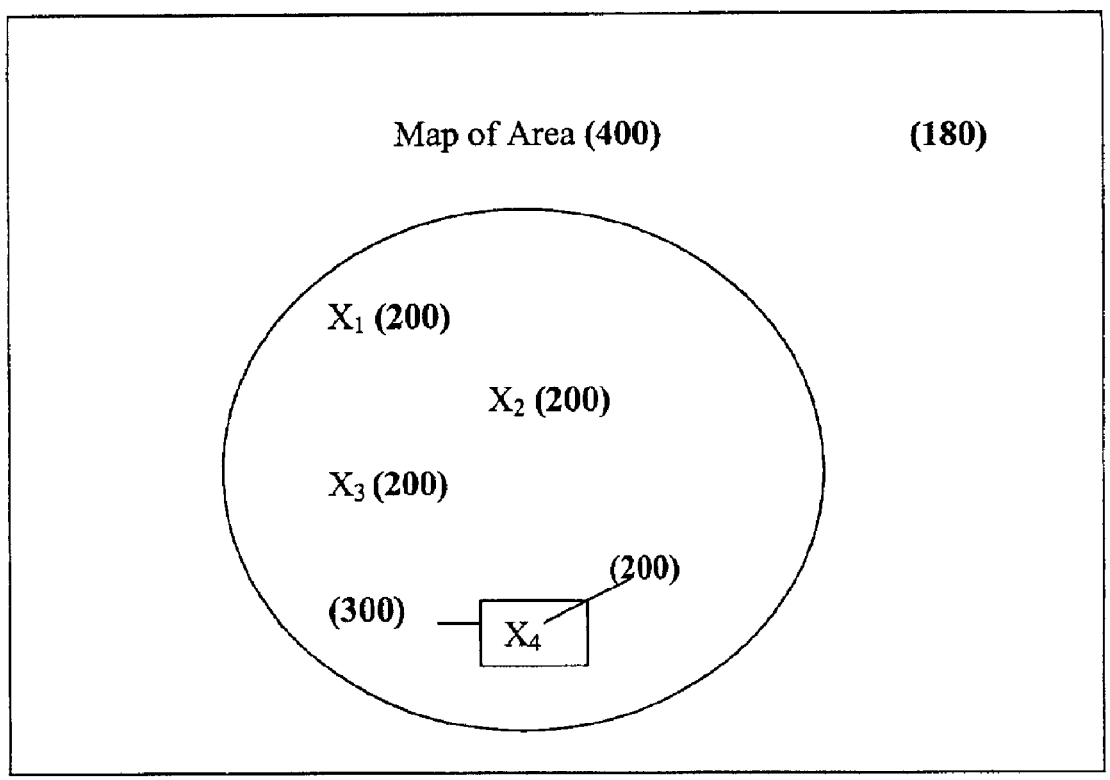
FIG. 9 shows an exemplary presentation of a map based interface utilized in the system of the present invention.
Figure 10:
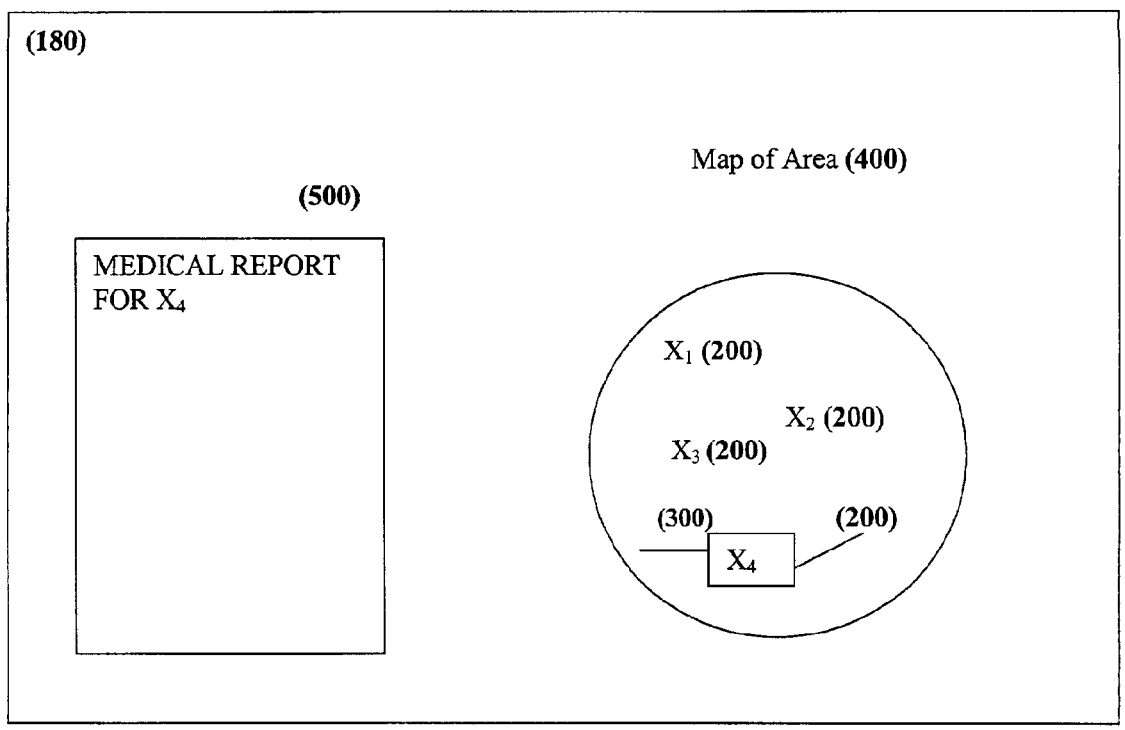
FIG. 10 shows an exemplary presentation of a map based interface and medical reporting scheme utilized in the system of the present invention.

For example, FIG. 8 shows an exemplary diagram of an embodiment of the present invention applied in a medical logistics application. Here, an epidemiologist wishes to send out a medical survey to all his health workers in the field to inquire about cases of Yellow Fever. The process begins with the creation of a medical survey. The epidemiologist uses Presentation Interface 180 to create a survey by way of Presentation Interface 120, Device Adapter 150, MSI 140, and finally the Survey Tool 174. The survey is a set of medical related questions formulated by the epidemiologist, that is then delivered to the health workers through the use of Communication Tool 168. The determination of the health workers to receive the survey, and by which device, is made by use of Contacts Tool 165. The survey is then delivered to each health worker through MSI 140, Device Adapter 150, and then through User Presentation Interface 110. The health worker may respond to the survey, and the results of the survey can be manipulated by Survey Tool 174 and stored in Information Source 190. Now, Telemetry Tool 164 may access a set of maps also stored in Information Source 190 and extract the location information for each of the health workers through Profiling Tool 163. Telemetry Tool 164 can then create a map of the location of all health workers who reported positive cases of Yellow Fever. This information is then presented to the epidemiologist who originated the survey through Management Presentation Interface 180. The epidemiologist is now able to see a geographical view of all the Yellow Fever cases. (See FIG. 9). FIG. 9 shows an exemplary presentation of a map based interface through MPI 180 where an "X" (200) on the map (400) represents the locations of health workers reporting positive cases of Yellow Fever. The epidemiologist can click on through Management Presentation Interface 180 a particular "X" (200) displayed on the map region (400) which in turn can display details on MPI 180 of the specific cases (500), as reported by the health worker. (See FIG. 10). Further, the epidemiologist can initiate communication with the specific health worker who reported a specific case of yellow fever through the use of Communication Tool 168 (using voice messaging for example). Thus, through the use of this Geographical Information System, the epidemiologist is able to effectively manage information through visual and data methods.

Supply Chain and Workflow Management Application

The present invention is also applicable in a number of environments involving supply chain and workflow management, including, but not limited to for instance, in the process of purchasing of a product, and its management through its life cycle. This application of the present invention is equally suitable if the product was substituted with an end user, or other system or process, and represents a very useful feature of the invention, as it combines typical workflow solutions with real time communication and collaboration mechanisms.

Figure 7:
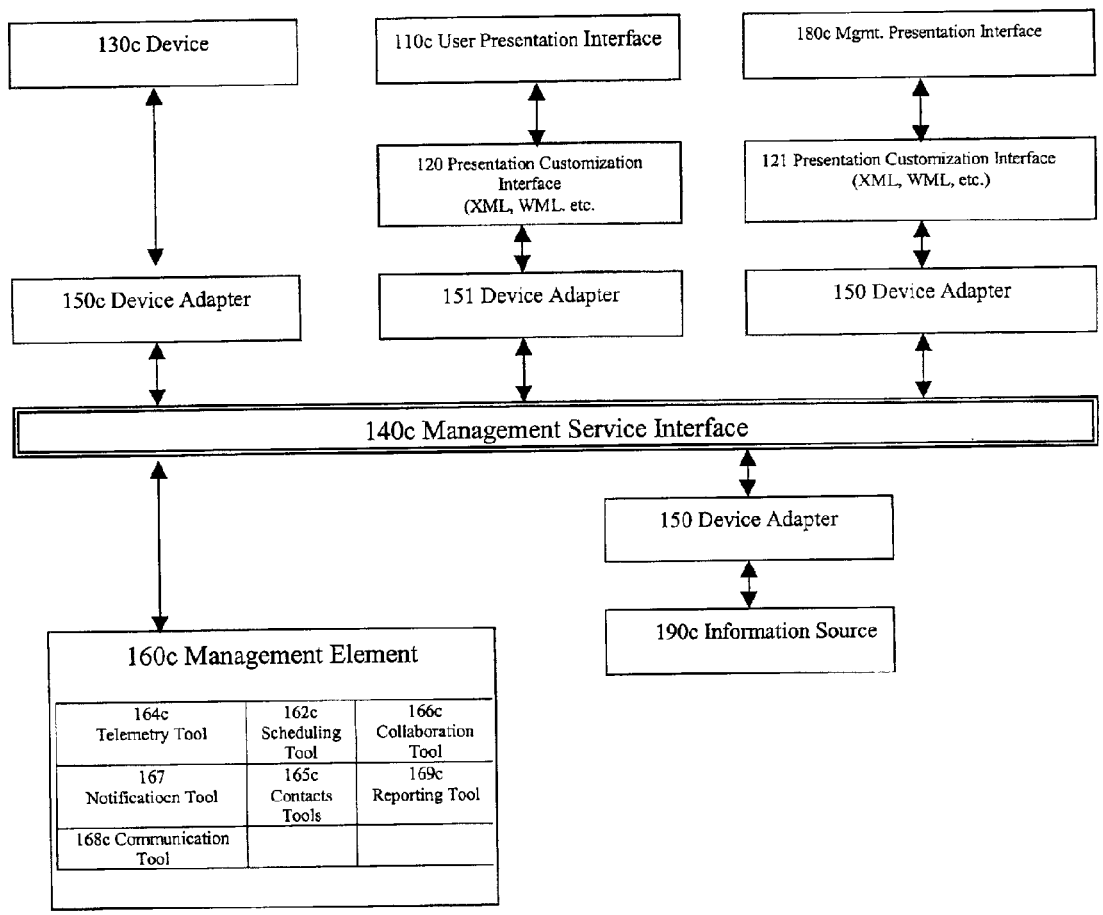
FIG. 7 shows a flow diagram of another embodiment of the voice and data based system contemplated by the present invention.

FIG. 7 shows an exemplary flow diagram of an embodiment of the present invention applied in a supply chain and work flow management environment. In this example, a product life cycle begins with the end user purchasing the product 130*c*. This can happen either directly through the manufacturer or reseller, or alternately through the UPI 110*c* via a suitable combination of tools in ML 160*c* (e.g., based on customer Profile information using 163*c*) or via 190*c*, which could be the manufacturer or reseller's sales channel.

When the end user purchases a product 130*c*, all user and product attributes that are relevant to the transaction are transmitted via 180*c*, and subsequently processed by 163*c* in 160*c*. Subsequently, the processed information is stored in 190*c* (e.g., a database or other repository). This information may also be sent to 110*c* for the end user's records, and to 180*c* for the seller's records. At this time, 166*c* is used to create a group, which comprises the end user, the device 130*c*, the seller of the product, and all other $3^{rd}$ parties that need to be associated with the transaction (e.g., suppliers of parts for the product, service center for servicing and repairing the product, etc.). Further, through 110*c*, the end user is given a way to add or remove people from the group, to suit their needs (e.g., choice of specific repair centers or parts suppliers based on the user's geographical location, etc.).

Telemetry tool 164*c* collect telemetry information from product 130*c* in one of two ways. First, if the product 130*c* is capable of communicating over the data network, it communicates via 150*c*, through 140*c*, and then to 164*c*. The information transmitted by the product 130*c* or requested by 164*c* is received in this fashion, and subsequently processed to extract relevant information. Secondly, if the product is not capable of communicating, information is then collected from the product 130*c* in more passive ways, such as for example, requesting the end user to periodically enter product related information via 110*c*, or by keeping track of periodic servicing date information for device 130*c* (as suggested by the manufacturer). This ensures that any time sensitive information pertaining to the product 130*c* is accurately tracked.

If any information handled by a component of 160*c* causes results in a request for notification or request for a time sensitive task to be performed, the request is managed by 167*c*. This component creates notification messages based on user and/or product profile (e.g., when and where a notification message is to be delivered, the format of the message etc.), and subsequently routes them through 168*c*.

Communication tool 168c manages all communication to and from the end user, and any seller, reseller or information source. For example, if 167c creates a notification message for an end user, and the message must be delivered as an electronic mail message, 168c manages the delivery of the message. If 168c needs an end user address to complete delivery, such information is managed by Contact Tool 165c.

Contact tool 165c manages a repository of all address and contact information, such as phone numbers, email addresses, pager numbers, or in the case of products or other information sources, particulars relating to the specifics of the product or information source in question. Contact tools 165c can be accessed by an end user via 110c, or by a seller, reseller or system manager via 160c, or by any other element of the system that has access to the 160c.

If product 130c has a problem, or needs repair or servicing, an event needs to be scheduled to service the product. Such events are scheduled by 162c. For example, if 164c gathers telemetry information that indicates a need for such an event, it communicates with 162c to set up an event schedule. This might involve communication with the end user via 110c as well communication with a repair agent represented accessible via 180c or Information Source 190c. Once all parties in the transaction agree on a date, 162c manages the date and timing of the event, and tracks its completion. This includes sending out reminders, or creating notification requests if the event needs to be re-scheduled or is overdue, etc. Similarly, for more passive events, such as, when product 130c's warranty is set to expire, 162c schedules notification requests, in order to indicate to the end user as well as other concerned parties of an upcoming warranty expiry event. This in turn may cause the end user to take action, such as applying for an extended warranty. Alternately, it might cause the seller of the product to contact the end user regarding new promotions, or new product models for sale, etc.

From time to time, an end user might want a report on some aspect of their product 130c or a multiplicity of products they own and operate. This might involve, for example, a historical summary of their products, or a history of repairs for their device. Alternately, a seller of products 130c might wish to collect some demographical information about end users 130c, or they might wish to see a repair history for 130c among all owners of the products (assuming the end users give them permission to see such information). Such requests are handled by 169c, which prepares the report, on the basis of requests received via 110c or 180c, or via 190c or in special cases, via a product such as 130c. Once a report is prepared, delivery of the report to the requester is handled via 168c.

In general, those skilled in the art will recognize that the present invention is not limited by the details described herein. Instead the present invention can be practiced with modifications and alterations within the spirit and scope of the appended claims. The description of the present invention is thus to be regarded as illustrative instead of restrictive in the present invention.

We claim:

1. A method for monitoring the condition of one or more individuals by one or more health care workers, the method comprising:

providing the one or more health care workers with at least one user device from among a plurality of non-identical user devices, each of the plurality of non-identical user devices being associated with at least one of a plurality of non-identical user interfaces, each of the plurality of user devices being communicatively linked to a device adapter enabling data to be adapted for use via each user device irrespective of associated user interface; said device adapter being communicatively linked to a system by a management service interface; said system comprising a management element for controlling one or more electronic tools within the system: each of said one or more electronic tools programmed to perform a desired function, said system further comprising one or more information sources for processing and storing information;

connecting the one or more health care workers to said system by the device adapter communicatively linked to the management service interface;

providing the one or more health care workers with one or more requests for information by sending said one or more requests through an interactive message interface extracted from the information source depending on a particular type of user device that is used by the one or more health care workers, the one or more health care workers entering the requested information in the system by way of the particular type of user device communicatively linked to the device adapter;

forwarding the requested information to a reporting tool;

processing the request information in a desired format by the reporting tool;

forwarding the processed information from the reporting tool to the information source to form at least one database; and providing a collaboration tool configured to enable one-to-one, one-to-many, many-to-one and many-to-many communications and collaborations among the one or more health care workers, the device adapter enabling use of the collaboration tool with said plurality of non-identical user devices irrespective of difference in workflow or collaborative contexts among the one or more health care workers or the plurality of non-identical user devices.

2. The method of claim 1, further comprising the steps of:

providing a communication tool programmed to authorize access into the system by the health care worker;

if the health care worker has one or more messages in the system, providing the health care worker means to retrieve said messages from the system by way of the user device.

3. The method of claim 1, further comprising the steps of:

providing a security tool programmed to authorize access into the system by the health care worker;

presenting the health care worker with an interactive voice response menu requiring the health care worker to input a pre-assigned authorized password by way of the user device;

the health care worker entering the authorized password in the system by way of the user device linked to the device;

forwarding the password to the security tool for determining if the password is authentic;

if the password is determined to be authentic by the security tool, providing the health care worker access to the system by way of the user device.

4. The method of claim 1, further comprising the steps of:

providing a survey tool for composing a medical survey to be forwarded to other health care workers having means to access the system;

composing a medical survey with the survey tool;

forwarding the medical survey to the user device by way of the management element to the device adapter.

5. The method of claim 1, further comprising the steps of:

providing a notification tool programmed to provide a predetermined notification function upon receiving a designated type of medical information pertaining to the condition of the one or more individuals;

forwarding the processed information from the reporting tool to the notification tool for determining whether such information contains any designated medical information;

if the processed information contains any designated information, delivering the designated information from the notification tool to a predetermined recipient.

6. The method of claim 1, further comprising the steps of:

providing a scheduling tool programmed to provide a predetermined message to the health care worker on a pre-selected date;

forwarding the predetermined message to the health care worker on the pre-selected date;

the predetermined message being forwarded to the health care worker by way of the management element to the device adapter.

7. The method of claim 1, further comprising the steps of:

providing a forecasting tool programmed to obtain a second set of medical information from the health care worker upon receiving a designated type of medical information pertaining to the condition of the one or more individuals;

forwarding the process information from the reporting tool to the forecasting tool for determining whether such information contain the designated medical information regarding the condition of the one or more individuals;

if the processed information contains any designated information, delivering a second set of requests for medical information from the health care worker by sending the requests to the user device by way of the management element to the device adapter.

8. The method of claim 1, further comprising the steps of;

providing a telemetry tool for collecting geographical data pertaining to the location of the user device as the user device accesses the system; and storing said geographical data in one or more information sources.

9. The method of claim 1, wherein the plurality of non-identical user devices include from a group consisting of telephones, palm pilots, personal computers, pagers, fax machines, wherein each of the plurality of non-identical device having a numbered keypad and the requested information is entered into the system by pressing one or more keys on the numbered key pad.

10. A health monitoring system for monitoring an individual or group of individual's condition by one or more health care workers, the system comprising:

a plurality of non-identical user devices, each of the plurality of non-identical devices being associated with at least one of a plurality of non-identical user interfaces, each of the plurality of user devices being communicatively linked to a device adapter enabling data to be adapted for use via each user device irrespective of associated user interface;

means for entering health information pertaining to the condition of said individual or group of individuals into at least one database depending on a particular type of user device that is used by the one or more health care workers;

means for accessing said health information pertaining to the one or more individuals represented in the at least one database;

processing means for processing said health information of at least one of said individuals with consideration of the health information in the at least one database;

means for retrieving the processed health information in a form whereby the healthcare worker practitioner is capable of identifying a condition in the individual or groups of individuals represented in the at least one database; and a collaboration tool configured to enable one-to-one, one-to-many, many-to-one and many-to-many communications and collaborations among the one or more health care workers, the device adapter enabling use of the collaboration tool with said plurality of non-identical user devices irrespective of difference in workflow or collaborative contexts among the one or more health care workers or the plurality of non-identical user devices.

11. The system of claim 10, wherein the means for processing the health information includes memory means for recording anatomical measurement for said individual or groups of individuals.

12. The system of claim 10, wherein the means for analysis further includes comparison means for comparing the recorded anatomical measurement with measurements stored in the memory means.

13. The system claim 10, wherein said processing means comprises:

a tool to automatically perform a categorizing function with respect to the information on said individual or groups of individuals represented in the at least one database; said categorizing function comprising categorizing said information based on the individual's sex, age, geographic location, weight, family background, blood pressure and heart rate.

means for retrieving the categorized information based on a predetermined parameter.

* * * * *